(12) United States Patent
Kameswaran

(10) Patent No.: US 6,320,059 B1
(45) Date of Patent: Nov. 20, 2001

(54) PROCESS FOR THE PREPARATION OF 2-ARYL-5-(PERFLUORO-ALKYL) PYRROLE COMPOUNDS FROM N-[1-CHLORO-1-(PERFLUOROALKYL) METHYL] ARYLIMIDOYL CHLORIDE COMPOUNDS

(75) Inventor: Venkataraman Kameswaran, Pennington, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/520,267

(22) Filed: Mar. 7, 2000

Related U.S. Application Data

(60) Provisional application No. 60/123,436, filed on Mar. 9, 1999.

(51) Int. Cl.[7] ............... C07D 207/32; C07D 207/34; C07D 207/00; C07D 207/30; C07D 207/323
(52) U.S. Cl. ............... 548/561; 548/517; 548/527; 548/531; 548/557; 548/562
(58) Field of Search ............... 548/561, 517, 548/527, 531, 557, 562

(56) References Cited

U.S. PATENT DOCUMENTS

| | | | |
|---|---|---|---|
| 5,010,098 | 4/1991 | Brown et al. | 514/426 |
| 5,145,986 | 9/1992 | Kameswaran et al. | 548/531 |
| 5,359,090 | 10/1994 | Doehner et al. | 548/561 |
| 5,426,225 | 6/1995 | Kameswaran | 564/212 |
| 5,446,170 | 8/1995 | Kameswaran | 548/517 |
| 5,449,789 | 9/1995 | Kameswaran | 548/561 |
| 5,817,834 | 10/1998 | Kameswaran | 548/561 |
| 5,965,773 | 10/1999 | Kameswaran | 564/272 |
| 6,011,161 | 1/2000 | Kameswaran | 548/560 |
| 6,133,455 | 10/2000 | Kameswaran | 548/517 |

FOREIGN PATENT DOCUMENTS

| | | | |
|---|---|---|---|
| 0934929 | 8/1999 | (EP) | C07D/207/34 |

OTHER PUBLICATIONS

Onys'ko, et al., "Sigmatropic Isomerizations In 2–AZA–Allylic Systems. Part X, Prototropic and Chlorotropic Rearrangements In Fluoroalkyl–Substituted 1,3–Dichloro–Imines", Journal of Flourine Chemistry, Elsevier Sequoia, Lausanne, CH, vol. 69, No. 3, 1994, pp. 213–218.

Faraci et al., "Mechanism Of Inactivation of Alanine Racemace By Beta, Beta, Beta–Trifluoralanine", Biochemistry, American Chemical Society. Easton, PA, vol. 28, No. 2, 1989 pp. 431–437.

Mustafa et al., "Trifluoropyruvic Acid Hydrate In Heterocyclic Synthesis Part III: A Novel Synthesis of 4–(Triflouromethyl)–Oxazolones and Other Related Compounds", Heterocycles, XX, XX, vol. 24, No. 6, 1986, pp. 1541–1547.

Tanaka et al, Bull. Chem. Soc. Japan, 66, pp. 661–663 (1993).

Tanaka et al, Chemistry Letters, pp. 1463–1464 (1983).

*Primary Examiner*—Floyd D. Higel
*Assistant Examiner*—Andrea M. D'Souza
(74) *Attorney, Agent, or Firm*—Charles F. Costello

(57) ABSTRACT

There is provided a process for the preparation of 2-aryl-5-(perfluoroalkyl)pyrrole compounds from N-[1-chloro-1-(perfluoroalkyl)methyl]arylimidoyl chloride compounds. The 2-aryl-5-(perfluoroalkyl)pyrrole compounds are useful for the control of insect and acrid pests, and may also be used to prepare other pesticidal arylpyrrole compounds.

In addition, the present invention provides compounds which are useful as intermediates in the preparation of arylpyrrole compounds.

11 Claims, No Drawings

PROCESS FOR THE PREPARATION OF 2-ARYL-5-(PERFLUORO-ALKYL) PYRROLE COMPOUNDS FROM N-[1-CHLORO-1-(PERFLUOROALKYL) METHYL] ARYLIMIDOYL CHLORIDE COMPOUNDS

This application claims benefit of Ser. No. 60/123,436 filed Mar. 9, 1999.

BACKGROUND OF THE INVENTION

2-Aryl-5-(perfluoroalkyl)pyrrole compounds are useful as insecticidal and acaricidal agents. In addition, those compounds are also useful for the preparation of other insecticidal and acaricidal agents. In particular, 2-aryl-5-(perfluoroalkyl)pyrrole compounds are key intermediates in the preparation of arylpyrrole compounds such as chlorfenapyr. Accordingly, there is an ongoing search to discover new methods for the preparation of 2-aryl-5-(perfluoroalkyl) pyrrole compounds.

U.S. Pat. No. 5,145,986 discloses that 2-aryl-5-(trifluoromethyl)pyrrole compounds may be prepared by reacting an N-(substituted benzyl)-2,2,2-trifluoroacetimidoyl chloride compound with an α-halo-α,β-unsaturated nitrile, ester or nitro compound in the presence of a base. However, the process described in U.S. Pat. No. 5,145,986 is not entirely satisfactory because the required α-halo-α,β-unsaturated nitrile, ester or nitro compound is prepared in a two step—halogenation/dehydrohalogenation—process.

U.S. Pat. Nos. 5,446,170 and 5,426,225 disclose that 2-aryl-5-(trifluoromethyl)pyrrole compounds may be obtained in several steps from the appropriate aldehyde. The processes described in U.S. Pat. Nos. 5,446,170 and 5,426,225 require the use of an aminonitrile intermediate which is obtained via the Strecker synthesis from the appropriate aldehyde. However, the use of the Strecker synthesis is not entirely satisfactory because of cyanide containing waste streams.

It is, therefore, an object of the present invention to provide a new process for the preparation of 2-aryl-5-(perfluoroalkyl)pyrrole compounds which avoids the use of (α-halo-α,β-unsaturated nitrile, ester and nitro compounds and the Strecker synthesis.

It is also an object of this invention to provide a new process for the preparation of arylpyrrole compounds such as chlorfenapyr.

A further object of the present invention is to provide new intermediate compounds which are useful in the processes described hereinbelow.

Those and other objects of the present invention will become more apparent from the detailed description thereof set forth below.

SUMMARY OF THE INVENTION

The present invention provides a new process for the preparation of 2-aryl-5-(perfluoroalkyl)pyrrole compounds having the structural formula I

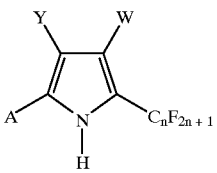

wherein

W is hydrogen or $C_mF_{2m+1}$;

Y is CN, $NO_2$ or $CO_2R$;

R is $C_1$–$C_4$alkyl;

m and n are each independently an integer of 1, 2, 3, 4, 5, 6, 7 or 8;

A is

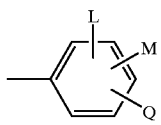

or

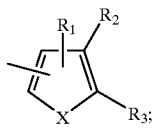

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfinyl, $C_1$–$C_4$haloalkylsulfinyl, $C_1$–$C_4$alkylsulfonyl, $C_1$–$C_4$haloalkylsulfonyl or when M and Q are on adjacent positions they may be taken together with the carbon atoms to which they are attached to form a ring in which MQ represents the structure —$OCH_2O$—, —$OCF_2O$— or —CH=CH—CH=CH—;

$R_1$, $R_2$ and $R_3$ are each independently hydrogen, halogen, $NO_2$, CHO or $R_2$ and $R_3$ may be taken together with the atoms to which they are a attached to form a ring in which $R_2R_3$ is represented by the structure

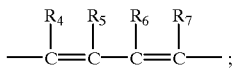

$R_4$, $R_5$, $R_6$ and $R_7$ are each independently hydrogen, halogen, CN or $NO_2$; and X is O or S, which process comprises reacting an N-[1-chloro-1-(perfluoroalkyl)methyl]arylimidoyl chloride compound having the structural formula II

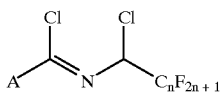 (II)

wherein A and n are as described above with a dieneophile compound having the structural formula III

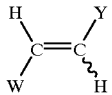 (III)

wherein W and Y are as described above and a base in the presence of a solvent.

The present invention further provides novel compounds having the structural formulas II, IV and V

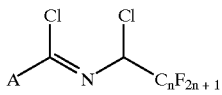 (II)

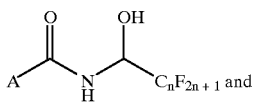 (IV)

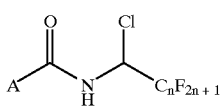 (V)

wherein n and A are as described hereinabove.

DETAILED DESCRIPTION OF THE INVENTION

The process of the present invention preferably comprises reacting an N-[1-chloro-1-(perfluoroalkyl)-methyl] arylimidoyl chloride compound of formula II with at least about one molar equivalent, preferably about one to four molar equivalents, of a dienophile compound of formula III and at least about one molar equivalent, preferably about one to four molar equivalents, of a base in the presence of a solvent preferably at a temperature range of about 5° C. to 100° C. to form 2-aryl-5-(perfluoroalkyl)pyrrole compounds of formula I.

Alternatively, the formula I compounds may be prepared by forming the formula III dienophile compounds in situ. This process comprises reacting an N-[1-chloro-1-(perfluoroalkyl)methyl]arylimidoyl chloride compound of formula II with preferably about one to four molar equivalents of a substituted haloethane compound having the structural formula VI

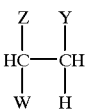 (VI)

wherein W and Y are as described hereinabove and Z is Cl, Br or I, and at least about two molar equivalents, preferably about two to five molar equivalents, of a base in the presence of a solvent preferably at a temperature range of about 5° C. 100° C. form 2-aryl-5-(perfluoroalkyl)pyrrole compounds of formula I.

Advantageously, the present invention provides new processes for the preparation of 2-aryl-5-(perfluoroalkyl) pyrrole compounds which avoid the use of α-halo-α,β-unsaturated nitrile, ester and nitro compounds and the Strecker synthesis.

The formula I compounds of this invention may be isolated by conventional procedures such as dilution of the reaction mixture with water and filtration or, alternatively, extraction with a suitable solvent. Suitable extraction solvents include water-immiscible solvents such as ether, ethyl acetate, toluene, methylene chloride and the like.

Bases suitable for use in this invention include tri-($C_1$–$C_6$alkyl)amines such as trimethylamine, triethylamine, tripropylamine, tributylamine, diisopropylethylamine and the like; alkali metal carbonates such as potassium carbonate and sodium carbonate; alkali metal hydroxides such as potassium hydroxide and sodium hydroxide; alkali metal acetates such as potassium acetate and sodium acetate; and heterocyclic tertiary amines including, but not limited to, 1,8-diazabicyclo[5.4.0]undec-7-ene (DBU); 1,5-diazabicyclo[4.3.0]non-5-ene (DBN); 1,4-diazabicyclo [2.2.2]-octane; pyridine; substituted pyridines such as 2,6-dimethylpyridine, 2-methylpyridine, 3-methylpyridine, 4-methylpyridine and the like; quinoline; and substituted quinolines. Preferred bases include tri-($C_1$–$C_6$alkyl)-amines, 1,8-diazabicyclo[5.4.0]undec-7-ene, 1,5-diazabicyclo[4.3.0] non-5-ene, 1,4-diazabicyclo[2.2.2]-octane, potassium carbonate and sodium carbonate.

Solvents suitable for use in the present invention include, but are not limited to, carboxylic acid amides such as N,N-dimethylformamide, N,N-dimethylacetamide and the like; N-substituted pyrrolidinones such as N-methylpyrrolidinone and the like; nitrites such as aceto-nitrile, propionitrile and the like; halogenated hydro-carbons such as methylene chloride, chloroform, carbon tetrachloride and the like; ethers such as tetrahydro-furan, dioxane and the like; sulfoxides such as dimethyl sulfoxide and the like; and mixtures thereof. Preferred solvents include carboxylic acid amides and nitrites and mixtures thereof. N,N-dimethylformamide and acetonitrile and mixtures thereof are especially preferred for use in the present invention.

Exemplary of halogen hereinabove are fluorine, chlorine, bromine and iodine. The terms $C_1$–$C_4$haloalkyl, $C_1$–$C_4$haloalkoxy, $C_1$–$C_4$haloalkylthio, $C_1$–$C_4$haloalkyl-sulfinyl and $C_1$–$C_4$haloalkylsulfonyl are defined as a $C_1$–$C_4$alkyl, $C_1$–$C_4$alkoxy, $C_1$–$C_4$alkylthio, $C_1$–$C_4$alkylsulfinyl or $C_1$–$C_4$alkylsulfonyl group substituted with one or more halogen atoms, respectively.

The present invention is especially useful for the preparation of formula I compounds wherein W is hydrogen;

Y is CN;

n is 1 or 2;

A is

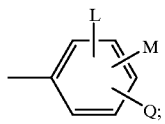

L is hydrogen or halogen; and

M and Q are each independently hydrogen, halogen, $C_1$–$C_4$haloalkyl or $C_1$–$C_4$haloalkoxy.

In particular, the present invention is useful for the preparation of 2-(p-chlorophenyl)-5-(trifluoromethyl)pyrrole-3-carbonitrile;

2-(p-bromophenyl)-5-(trifluoromethyl)pyrrole-3-carbonitrile;

2-(3,5-dichlorophenyl)-5-(trifluoromethyl)pyrrole-3-carbonitrile;

2-(3,4,5-trichlorophenyl)-5-(trifluoromethyl)pyrrole-3-carbonitrile; and

2-[4-(trifluoromethyl)phenyl]-5-(trifluoromethyl)pyrrole-3-carbonitrile, among others.

The present invention also relates to N-[1-chloro-1-(perfluoroalkyl)methyl]arylimidoyl chloride compounds having the structural formula II

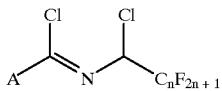

(II)

wherein n is an integer of 1, 2, 3, 4, 5, 6, 7 or 8;

A is

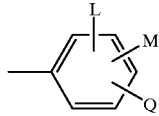

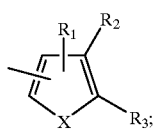

or

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfinyl, $C_1$–$C_4$haloalkylsulfinyl, $C_1$–$C_4$alkylsulfonyl, $C_1$–$C_4$haloalkylsulfonyl or when M and Q are on adjacent positions they may be taken together with the carbon atoms to which they are attached to form a ring in which MQ represents the structure —$OCH_2O$—, —$OCF_2O$— or —CH═CH—CH═CH—;

$R_1$, $R_2$ and $R_3$ are each independently hydrogen, halogen, $NO_2$, CHO or $R_2$ and $R_3$ may be taken together with the atoms to which they are attached to form a ring in which $R_2R_3$ is represented by the structure

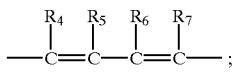

$R_4$, $R_5$, $R_6$ and $R_7$ are each independently hydrogen, halogen, CN or $NO_2$; and X is O or S.

Preferred formula II compounds of this invention are those wherein n is 1 or 2;

A is

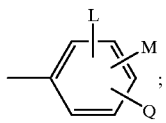

L is hydrogen or halogen; and

M and Q are each independently halogen, $C_1$–$C_4$haloalkyl or $C_1$–$C_4$haloalkoxy.

Formula II compounds which are particularly useful in the processes of this invention include N-[1-chloro-(2,2,2-trifluoroethyl)]-4-chlorobenzimidoyl chloride;

N-[1-chloro-(2,2,2-trifluoroethyl)]-4-bromobenzimidoyl chloride;

N-[1-chloro-(2,2,2-trifluoroethyl)]-3,5-dichlorobenzimidoyl chloride;

N-[1-chloro-(2,2,2-trifluoroethyl)]-3,4,5-trichlorobenzimidoyl chloride; and

N-[1-chloro-(2,2,2-trifluoroethyl)]-4-(trifluoromethyl)benzimidoyl chloride, among others.

Starting N-[1-chloro-1-(perfluoroalkyl)methyl]-arylimidoyl chloride compounds of formula II may be prepared, as shown in Flow Diagram I, by reacting an arylamide compound having the structural formula VII with a (perfluoroalkyl)aldehyde $C_1$–$C_6$alkyl hemiacetal compound having the structural formula VIII to form an N-[1-hydroxy-1-(perfluoroalkyl)methyl]arylamide compound having the structural formula IV, and reacting the formula IV compound with phosphorus pentachloride.

FLOW DIAGRAM I

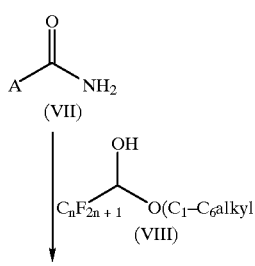

-continued

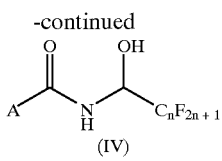
(IV)

↓ PCl$_5$

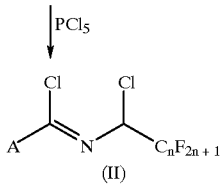
(II)

Alternatively, N-[1-chloro-1-(perfluoroalkyl)-methyl]arylimidoyl chloride compounds of formula II may be prepared, as shown in Flow Diagram II, by reacting an N-[1-hydroxy-1-(perfluoroalkyl)methyl]arylamide of formula IV with phosphorus trichloride to form an N-[1-chloro-1-(perfluoroalkyl)methyl]arylamide compound having the structural formula V, and reacting the formula V compound with phosphorus pentachloride.

FLOW DIAGRAM II

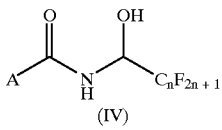
(IV)

↓ PCl$_3$

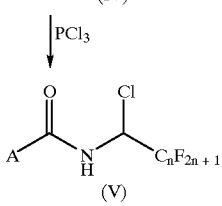
(V)

↓ PCl$_5$

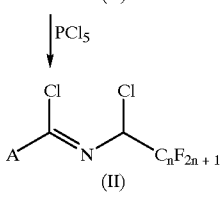
(II)

The present invention also relates to the formula IV and V compounds which are used to prepare the formula II compounds. In particular, the present invention provides N-[1-hydroxy-1-(perfluoroalkyl)methyl]arylamide compounds having the structural formula IV and N-[1-chloro-1-(perfluoroalkyl)methyl]arylamide compounds having the structural formula V

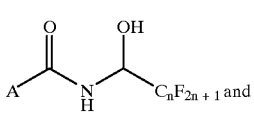
(IV)

-continued

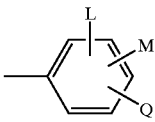
(V)

wherein
n is an integer of 1, 2, 3, 4, 5, 6, 7 or 8;
A is

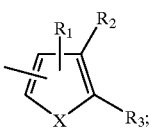

or

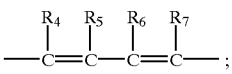

L is hydrogen or halogen;
M and Q are each independently hydrogen, halogen, CN, NO$_2$, C$_1$–C$_4$alkyl, C$_1$–C$_4$haloalkyl, C$_1$–C$_4$alkoxy, C$_1$–C$_4$haloalkoxy, C$_1$–C$^4$alkylthio, C$_1$–C$_4$haloalkylthio, C$_1$–C$_4$alkylsulfinyl, C$_1$–C$_4$haloalkylsulfinyl, C$_1$–C$_4$alkylsulfonyl, C$_1$–C$_4$haloalkylsulfonyl or when M and Q are on adjacent positions they may be taken together with the carbon atoms to which they are attached to form a ring in which MQ represents the structure —OCH$_2$O—, —OCF$_2$O— or —CH=CH—CH=CH—;
R$_1$, R$_2$ and R$_3$ are each independently hydrogen, halogen, NO$_2$, CHO or R$_2$ and R$_3$ may be taken together with the atoms to which they are attached to form a ring in which R$_2$R$_3$ is represented by the structure $$-\underset{R_4}{C}=\underset{R_5}{C}-\underset{R_6}{C}=\underset{R_7}{C}-\ ;$$

R$_4$, R$_5$, R$_6$ and R$_7$ are each independently hydrogen, halogen, CN or NO$_2$; and
X is O or S.

Preferred formula IV and V compounds of this invention are those wherein
n is 1 or 2;
A is

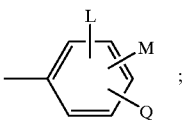

L is hydrogen or halogen; and
M and Q are each independently halogen, C$_1$–C$_4$haloalkyl or C$_1$–C$_4$haloalkoxy.

Formula IV compounds which are particularly useful for the preparation of arylpyrrole compounds include N-(1-hydroxy-2,2,2-trifluoroethyl)-4-chlorobenzamide;
N-(1-hydroxy-2,2,2-trifluoroethyl)-4-bromobenzamide;
N-(1-hydroxy-2,2,2-trifluoroethyl)-3,5-dichlorobenzamide;
N-(1-hydroxy-2,2,2-trifluoroethyl)-3,4,5-trichlorobenzamide; and
N-(1-hydroxy-2,2,2-trifluoroethyl)-4-(trifluoromethyl)benzamide, among others.

Formula V compounds which are particularly useful for the preparation of arylpyrrole compounds include
N-(1-chloro-2,2,2-trifluoroethyl)-4-chlorobenzamide;
N-(1-chloro-2,2,2-trifluoroethyl)-4-bromobenzamide;
N-(1-chloro-2,2,2-trifluoroethyl)-3,5-dichlorobenzamide;
N-(1-chloro-2,2,2-trifluoroethyl)-3,4,5-trichlorobenzamide; and
N-(1-chloro-2,2,2-trifluoroethyl)-4-(trifluoromethyl)benzamide, among others.

The formula I compounds are useful for the control of insect and acrid pests. In addition, the formula I compounds may be used to prepare other arylpyrrole insecticidal and acaricidal agents having the structural formula IX

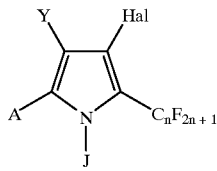

(IX)

wherein

Y is CN, NO$_2$ or CO$_2$R;

R is C$_1$–C$_4$alkyl;

n is an integer of 1, 2, 3, 4, 5, 6, 7 or 8;

A is

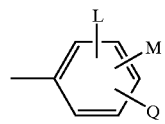

or

L is hydrogen or halogen;

M and Q are each independently hydrogen, halogen, CN, NO$_2$, C$_1$–C$_4$alkyl, C$_1$–C$_4$haloalkyl, C$_1$–C$_4$alkoxy, C$_1$–C$_4$haloalkoxy, C$_1$–C$_4$alkylthio, C$_1$–C$_4$haloalkylthio, C$_1$–C$_4$alkylsulfinyl, C$_1$–C$_4$haloalkylsulfinyl, C$_1$–C$_4$alkylsulfonyl, C$_1$–C$_4$haloalkylsulfonyl or when M and Q are on adjacent positions they may be taken together with the carbon atoms to which they are attached to form a ring in which MQ represents the structure —OCH$_2$O—, —OCF$_2$O— or —CH=CH—CH=CH—;

R$_1$, R$_2$ and R$_3$ are each independently hydrogen, halogen, NO$_2$, CHO or R$_2$ and R$_3$ may be taken together with the atoms to which they are attached to form a ring in which R$_2$R$_3$ is represented by the structure

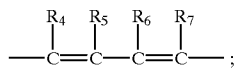

R$_4$, R$_5$, R$_6$ and R$_7$ are each independently hydrogen, halogen, CN or NO$_2$;

X is O or S;

Hal is a halogen atom; and

J is hydrogen or C$_1$–C$_6$alkoxymethyl.

The present invention is especially useful for the preparation of arylpyrrole compounds of formula IX wherein Y is CN;

n is 1 or 2;

A is

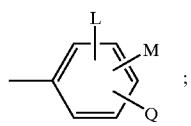

L is hydrogen or halogen;

M and Q are each independently hydrogen, halogen, C$_1$–C$_4$haloalkyl or C$_1$–C$_4$haloalkoxy;

Hal is Br or Cl; and

J is hydrogen or ethoxymethyl.

In particular, the present invention is useful for the preparation of formula IX arylpyrrole compounds such as 4-bromo-2-(p-chlorophenyl)-1-(ethoxymethyl)-5-(trifluoromethyl)pyrrole-3-carbonitrile, (chlorfenapyr);

4-bromo-2-(3,5-dichlorophenyl)-1-(ethoxymethyl)-5-(trifluoromethyl)pyrrole-3-carbonitrile;

4-bromo-2-(3,5-dichlorophenyl)-5-(trifluoromethyl)pyrrole-3-carbonitrile; and 4-bromo-2-(p-chlorophenyl)-5-(trifluoromethyl)pyrrole-3-carbonitrile, among others.

Advantageously, formula IX arylpyrrole compounds may be prepared by a process which comprises:

(a) reacting an N-[1-chloro-1-(perfluoroalkyl)methyl] arylimidoyl chloride compound of formula II with a dienophile compound having the structural formula X

(X)

(X) wherein Y is as described above and a base in the presence of a solvent to form a 2-aryl-5-(perfluoroalkyl)pyrrole compound having the structural formula XI

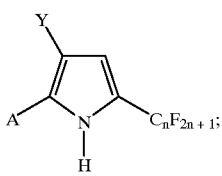

(XI)

(b) halogenating the formula XI compound to form the arylpyrrole compound of formula IX wherein J is hydrogen; and
(c) optionally alkoxymethylating the formula IX compound wherein J is hydrogen to form the formula IX arylpyrrole compound wherein J is $C_1$–$C_6$alkoxymethyl.

Alternatively, arylpyrrole compounds of formula IX may be prepared by a process which comprises:

(a) reacting an N-[1-chloro-1-(perfluoroalkyl)-methyl] arylimidoyl chloride compound of formula II with a substituted haloethane compound having the structural formula XII

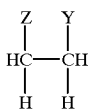

(XII)

wherein Y is as described above and Z is Cl, Br or I, and at least about two molar equivalents of a base in the presence of a solvent to form a 2-aryl-5-(perfluoroalkyl)pyrrole compound having the structural formula XI

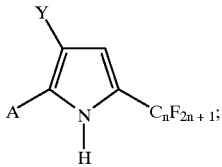

(XI)

(b) halogenating the formula XI compound to form the arylpyrrole compound of formula IX wherein J is hydrogen; and
(c) optionally alkoxymethylating the formula IX compound wherein J is hydrogen to form the formula IX arylpyrrole compound wherein J is $C_1$–$C_6$alkoxymethyl.

Halogenation methods may be any known methods such as those described in U.S. Pat. Nos. 5,010,098 and 5,449,789.

Alkoxymethylation procedures suitable for use in this invention include conventional procedures known in the art (see, e.g., U.S. Pat. Nos. 5,010,098 and 5,359,090). In a preferred embodiment of this invention, the alkoxymethylation procedure comprises reacting a formula IX compound wherein J is hydrogen with a di-($C_1$–$C_6$alkoxy)methane compound, N,N-dimethylformamide and phosphorous oxychloride in the presence of an aprotic solvent to form a reaction mixture and treating the reaction mixture with a tertiary amine.

In order to facilitate a further understanding of this invention, the following examples are presented primarily for the purpose of illustrating more specific details thereof. The scope of the invention should not be deemed limited by the examples, but encompasses the entire subject matter defined in the claims.

EXAMPLE 1

Preparation of N-(1-Hydroxy-2,2,2-trifluoroethyl)-4-chlorobenzamide

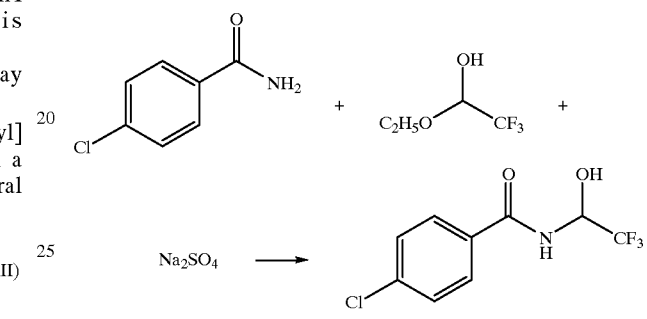

A solution of 4-chlorobenzamide (22.0 g, 0.141 mol) and trifluoroacetaldehyde ethyl hemiacetal (25.0 g as is, 22.5 g real, 0.156 mol) in dioxane (200 mL) is treated with anhydrous sodium sulfate (10 g, to dry the 10% water in the hemiacetal) and refluxed for 60 hours. The solids are filtered and the filtrate is evaporated to a solid. The solids are dissolved in about 200 mL of 15% ethyl acetate in heptane. Unreacted starting material (5.6 g) crystallizes out and is filtered. The title product is obtained from the mother liquors as a white crystalline solid (22.1 g, 82.9% based on recovery of starting material): mp 139.5–140.5° C.; characterized by $^1$H and $^{19}$F NMR and Mass spectra. $^1$H NMR (DMSO-$d_6$) δ 9.45 (d, J=8.7 Hz, NH), 7.93, 7.54 (AB with fine splitting, J=8.4 Hz, ArH), 7.54 (broad s, OH), 5.90 (m, J=8.7, 2.9, 5.8 Hz, CH); $^{19}$F NMR δ –80.3 (d, J=5 Hz).

Following essentially the same procedure, but using the appropriately substituted benzamide, the following compounds are obtained:

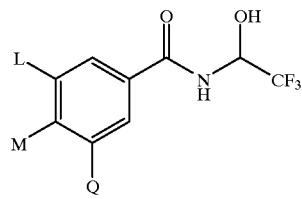

| L | M | Q | mp ° C. |
|---|---|---|---|
| Cl | H | Cl | 152.5–153 |
| H | Br | H | 148–148.5 |
| H | CF$_3$ | H | 124–124.5 |

EXAMPLE 2

Preparation of N-[1-Chloro-(2,2,2-trifluoroethyl)]-4-chlorobenzimidoyl chloride

METHOD A

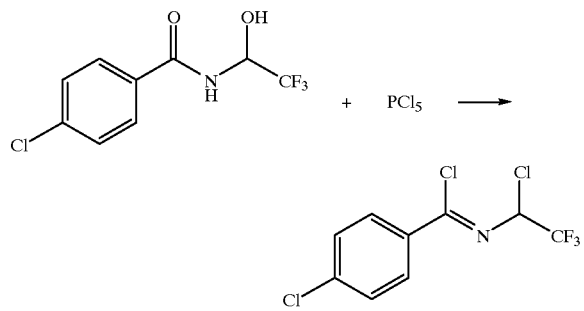

A mixture of N-(1-hydroxy-2,2,2-trifluoroethyl)-4-chlorobenzamide (22.1 g, 0.087 mol) in phosphorus oxychloride (8 mL) is treated with phosphorus pentachloride (40.0 g, 0.192 mol), heated to and held at 100° C. for 15–20 minutes, cooled, and concentrated in vacuo to obtain a residue. The residue is distilled to give the title product as a clear liquid (22.2 g, 87.8% yield): bp 77–78° C. (0.1 mm); characterized by IR, $^1$H and $^{19}$F NMR, and Mass spectra. $^1$H NMR (CDCl$_3$) δ 8.06, 7.44 (d with fine splitting, J=8.9 Hz, ArH), 5.92 (q, J=4.9 Hz, CH); $^{19}$F NMR δ −77.9 (d, J=5 Hz)

METHOD B

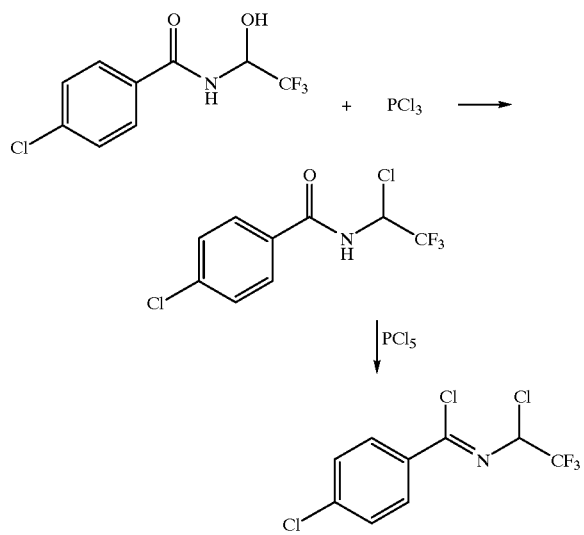

A mixture of N-(1-hydroxy-2,2,2-trifluoroethyl)-4-chlorobenzamide (16.3 g, 0.064 mol) in phosphorus oxychloride (10 mL) is treated with phosphorus trichloride (9.3 g, 0.675 mol) and heated to and held at 80° C. for 15–20 minutes. $^{19}$F NMR shows clean and complete conversion to N-(1-chloro-2,2,2-trifluoroethyl)-4-chlorobenzamide. The reaction mixture is then cooled to room temperature, treated with phosphorus pentachloride (28.0 g, 0.135 mol), and heated to and held at 100° C. for 1 hour. The phosphorus oxychloride is then removed in vacuo and the resultant residue is vacuum distilled to give the title product as a clear liquid (18.5 g, 1000 yield): bp 94–96° C. (0.5 mm).

Following essentially the same procedure as described in Method A, but using the appropriately substituted N-(1-hydroxy-2,2,2-trifluoroethyl)-4-benzamide, the following compounds are obtained:

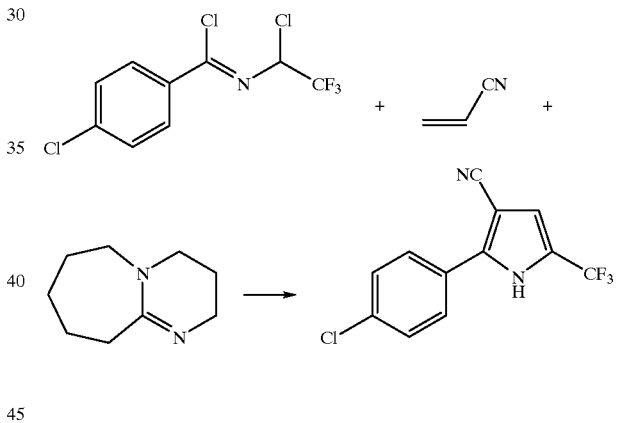

| L  | M   | Q  | bp              |
|----|-----|----|-----------------|
| Cl | H   | Cl | 114° C. (0.3 mm)  |
| H  | Br  | H  | 95–96° C. (0.07 mm) |
| H  | CF$_3$ | H  | waxy solid      |

EXAMPLE 3

Preparation of 2-(p-Chlorophenyl)-5-(trifluoromethyl)pyrrole-3-carbonitrile

A solution of N-[1-chloro-(2,2,2-trifluoroethyl)]-4-chlorobenzimidoyl chloride (5.80 g, 0.02 mol) and acrylonitrile (1.33 g, 0.025 mol) in N,N-dimethyl-formamide (15 mL) is treated with 1,8-diazabicyclo-[5.4.0]undec-7-ene (DBU, 8.53 g, 0.056 mol) over 1 hour while maintaining the temperature at 45°–50° C. The reaction mixture is then stirred at 50° C. for 4 hours, quenched with dilute HCl, and extracted with ethyl acetate. The organic extract is concentrated in vacuo to obtain a residue. Flash chromatography of the residue on silica gel, packed and eluted with 20% ethyl acetate in heptane, and crystallization from heptane and small amount of ethyl acetate gives the title product as a white crystalline solid (2.1 g, 38.9% yield): mp 239–240° C. (dec).

Following essentially the same procedure, but using the appropriately substituted N-[1-chloro-(2,2,2-trifluoroethyl)] benzimidoyl chloride, the following compounds are obtained:

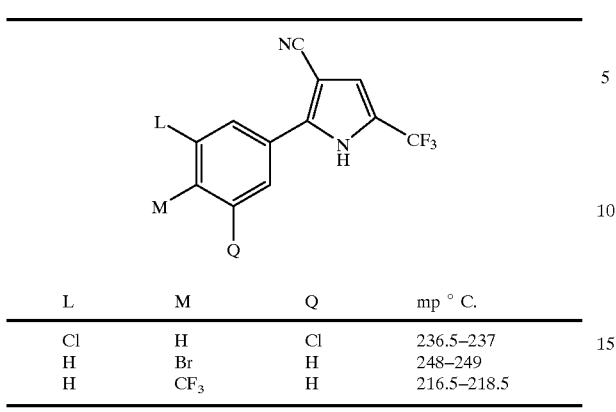

| L  | M   | Q  | mp ° C.     |
|----|-----|----|-------------|
| Cl | H   | Cl | 236.5–237   |
| H  | Br  | H  | 248–249     |
| H  | CF3 | H  | 216.5–218.5 |

EXAMPLE 4

Preparation of Methyl 2-(4-chlorophenyl)-5-(trifluoromethyl)pyrrole-3-carboxylate

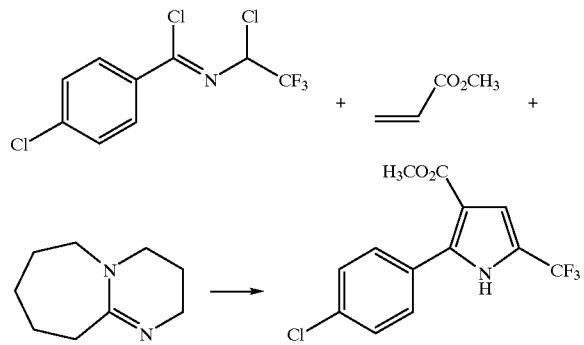

A solution of N-[1-chloro-(2,2,2-trifluoroethyl)]-4-chlorobenzimidoyl chloride (3.40 g, 0.012 mol) and methyl acrylate (1.26 g, 0.015 mol) in N,N-dimethylformamide (10 mL) is treated with 1,8-diazabicyclo[5.4.0]undec-7-ene (DBU, 5.0 g, 0.033 mol) over 1 hour. The reaction mixture is then held at 600° C. for 15 minutes, quenched with dilute HCl, and extracted with ethyl acetate. The organic extract is concentrated in vacuo to obtain a residue. Flash chromatography of the residue on silica gel, packed and eluted with 20% ethyl acetate in heptane, and crystallization from heptane gives the title product as a yellow solid (0.95 g, 26.0% yield) which is identified by $^1$H and $^{19}$F NMR spectral analyses.

EXAMPLE 5

Preparation of 4-Bromo-2-(4-chlorophenyl)-5-(trifluoromethyl)pyrrole-3-carbonitrile

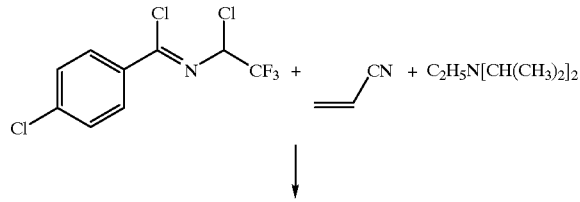

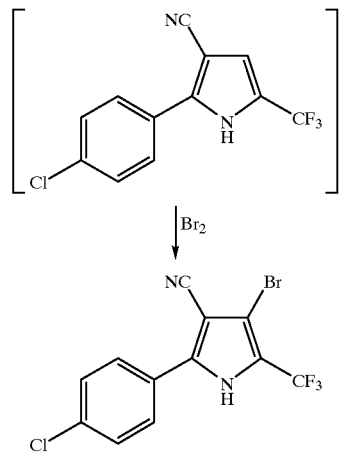

A solution of N-[1-chloro-(2,2,2-trifluoroethyl)]-4-chlorobenzimidoyl chloride (5.80 g, 0.02 mol) and acrylonitrile (1.33 g, 0.025 mol) in N,N-dimethyl-formamide (15 mL) under a nitrogen atmosphere is treated with N,N-diisopropylethylamine (DIPEA, 7.8 g, 0.06 mol) over 30 minutes, heated to and held at 45–47° C. for 18 hours, cooled to room temperature, treated with bromine (3.2 g, 0.02 mol), stirred at room temperature for 1 hour, quenched with water, and extracted with ethyl acetate. The organic extract is concentrated in vacuo to obtain a residue. Flash column chromatography of the residue on silica gel, packed with 15% ethyl acetate in heptane and eluted with 20% ethyl acetate in heptane, gives the title product as white solid (1.6 g, 22.9% yield) which is identified by $^1$H and $^{19}$F NMR spectral analyses.

EXAMPLE 6

Preparation of N-(1-Chloro-2,2,2-trifluoroethyl)-4-chlorobenzamide

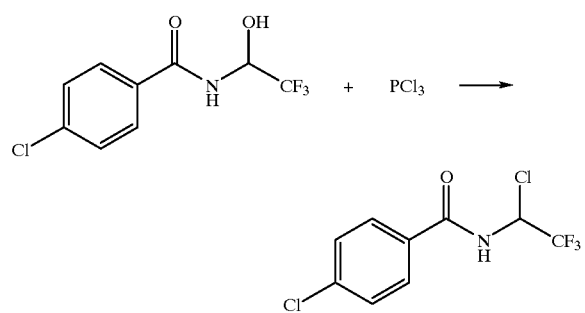

A mixture of N-(1-hydroxy-2,2,2-trifluoroethyl)-4-chlorobenzamide (2.53 g, 0.01 mol) in phosphorus oxychloride (2 mL) is treated with phosphorus trichloride (1.57 g, 0.012 mol), heated to and held at 80° C. for 30 minutes, and concentrated in vacuo to obtain a residue. The residue is dissolved in hot heptane, decanted from the waxy phosphorus products, and crystallized to give the title product as a white crystalline solid (2.43 g, 89.3% yield): mp 119.0–121.0° C.; IR (Nujol) 3266, 1668 cm$^{-1}$; $^1$H NMR (CDCl$_3$) δ 7.76 and 7.46 (AB with fine splitting, ArH), 6.86 (d, J=8.5 Hz, NH, moves to 10.24 in DMSO-d$_6$), 6.55(m, CH); $^{19}$F NMR δ −77.7(d, J=5 Hz).

Following essentially the same procedure, but using the appropriately substituted N-(1-hydroxy-2,2,2-trifluoroethyl)benzamide, the following compounds are obtained:

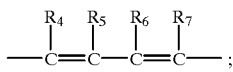

| L  | M   | Q  | mp ° C.     |
|----|-----|----|-------------|
| Cl | H   | Cl | 163.5–164   |
| H  | Br  | H  | 135–136.5   |
| H  | CF$_3$ | H  | 122.5–123.5 |

I claim:
1. A process for the preparation of a 2-aryl-5-(perfluoroalkyl)pyrrole compound having the formula I

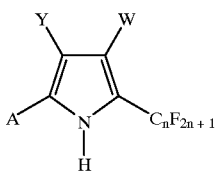 (I)

wherein
W is hydrogen or $C_mF_{2m+1}$;
Y is CN, NO$_2$ or CO$_2$R;
R is C$_1$–C$_4$alkyl;
m and n are each independently an integer of 1, 2, 3, 4, 5, 6, 7 or 8;
A is

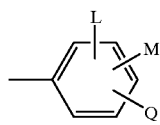

or

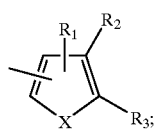

L is hydrogen or halogen;
M and Q are each independently hydrogen, halogen, CN, NO$_2$, C$_1$–C$_4$alkyl, C$_1$–C$_4$haloalkyl, C$_1$–C$_4$alkoxy, C$_1$–C$_4$haloalkoxy, C$_1$–C$_4$alkylthio, C$_1$–C$_4$haloalkylthio, C$_1$–C$_4$alkylsulfinyl, C$_1$–C$_4$haloalkylsulfinyl, C$_1$–C$_4$alkylsulfonyl or C$_1$–C$_4$haloalkylsulfonyl, or when M and Q are on adjacent positions they may be taken together with the carbon atoms to which they are attached to form a ring in which MQ represents the structure —OCH$_2$O—, —OCF$_2$O— or —CH=CH—CH=CH—;

R$_1$, R$_2$ and R3 are each independently hydrogen, halogen, NO$_2$ or CHO, or R$_2$ and R$_3$ may be taken together with the atoms to which they are attached to form a ring in which R$_2$R$_3$ is represented by the structure

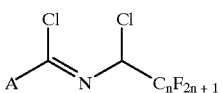

R$_4$, R$_5$, R$_6$ and R$_7$ are each independently hydrogen, halogen, CN or NO$_2$; and
X is O or S,
which process comprises reacting an N-[1-chloro-1-(perfluoroalkyl)methyl]arylimidoyl chloride compound having the formula II

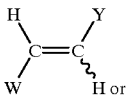 (II)

wherein A and n are as described above, with a dieneophile compound or a substituted haloethane compound, and a base, in the presence of a solvent, the dieneophile compound having the formula III and the substituted haloethane compound having the formula VI

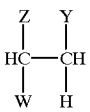 (III)

(IV)

wherein W and Y are as described above, and Z is Cl, Br or I.

2. The process according to claim 1 wherein the base is selected from the group consisting of a tri-(C$_1$–C$_6$alkyl)amine, an alkali metal carbonate and a heterocyclic tertiary amine.

3. The process according to claim 2 wherein the base is selected from the group consisting of a tri-(C$_1$–C$_6$alkyl)amine, 1,8-diazabicyclo[5.4.0]undec-7-ene, 1,5-diazabicyclo[4.3.0]non-5-ene, 1,4-diazabicyclo[2.2.2]octane, potassium carbonate and sodium carbonate.

4. The process according to claim 3 wherein the tri-(C$_1$–C$_6$alkyl)amine is selected from the group consisting of trimethylamine, triethylamine, tripropylamine, tributylamine and diisopropylethylamine.

5. The process according to claim 1 wherein the solvent is selected from the group consisting of a carboxylic acid amide and a nitrile, and mixtures thereof.

6. The process according to claim 5 wherein the solvent is selected from the group consisting of N,N-dimethylformamide and acetonitrile, and mixtures thereof.

7. The process according to claim 1 wherein the dieneophile is at about one to four molar equivalents and the base is at about one to four molar equivalents.

8. The process according to claim 1 wherein the substituted haloethane compound is at about one to four molar equivalents and the base is present in the amount of about two to five molar equivalents.

9. The process according to claim 1 wherein
W is hydrogen;
Y is CN;
n is 1 or 2;
A is

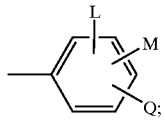

L is hydrogen or halogen; and
M and Q are each independently hydrogen, halogen, $C_1$–$C_4$haloalkyl or $C_1$–$C_4$haloalkoxy.

10. A process for the preparation of an arylpyrrole compound having the formula IX

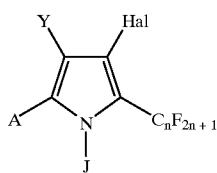

(IX)

wherein
Y is CN, $NO_2$ or $CO_2R$;
R is $C_1$–$C_4$alkyl;
n is an integer of 1, 2, 3, 4, 5, 6, 7 or 8;
A is

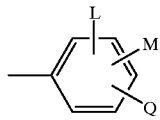

or

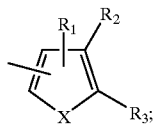

L is hydrogen or halogen;
M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfinyl, $C_1$–$C_4$haloalkylsulfinyl, $C_1$–$C_4$alkylsulfonyl or $C_1$–$C_4$haloalkylsulfonyl, or when M and Q are on adjacent positions they may be taken together with the carbon atoms to which they are attached to form a ring in which MQ represents the structure —$OCH_2O$—, —$OCF_2O$— or —CH=CH—CH=CH—;
$R_1$, $R_2$ and $R_3$ are each independently hydrogen, halogen, $NO_2$ or CHO, or $R_2$ and $R_3$ may be taken together with the atoms to which they are attached to form a ring in which $R_2R_3$ is represented by the structure

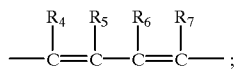

$R_4$, $R_5$, $R_6$ and $R_7$ are each independently hydrogen, halogen, CN or $NO_2$;
X is O or S;
Hal is a halogen atom; and
J is hydrogen or $C_1$–$C_6$alkoxymethyl, which process comprises:
(a) reacting an N-[1-chloro-1-(perfluoroalkyl)methyl] arylimidoyl chloride compound having the formula II

(II)

wherein A and n are as described above, with a dieneophile compound or a substituted haloethane compound, and a base, in the presence of a solvent, the dieneophile compound having the formula X and the substituted haloethane compound having the formula XII

(X)

(XII)

wherein Y is as described above, and Z is Cl, Br or I, to form a 2-aryl-5-(perfluoroalkyl)pyrrole compound having the formula XI

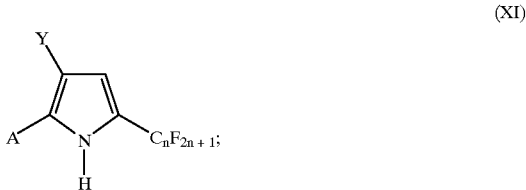

(XI)

(b) halogenating the formula XI compound to form the arylpyrrole compound of formula IX wherein J is hydrogen; and
(c) optionally alkoxymethylating the formula IX compound.

11. The process according to claim 10 wherein step (c) comprises reacting said formula IX compound with a di-($C_1$–$C_6$alkoxy)methane compound, N,N-dimethylformamide and phosphorous oxychloride in the presence of an aprotic solvent to form a reaction mixture, and treating the reaction mixture with a tertiary amine.

* * * * *